United States Patent [19]

Kessel

[11] Patent Number: 4,861,876
[45] Date of Patent: Aug. 29, 1989

[54] HEMATOPORPHYRIN DERIVATIVE AND METHOD OF PREPARATION AND PURIFICATION

[75] Inventor: David Kessel, Detroit, Mich.
[73] Assignee: Wayne State University, Detroit, Mich.
[21] Appl. No.: 935,269
[22] Filed: Nov. 26, 1986
[51] Int. Cl.⁴ .......................................... C07D 487/22
[52] U.S. Cl. .................................................. 540/145
[58] Field of Search ....................................... 540/145

[56] References Cited

U.S. PATENT DOCUMENTS 4,649,151  3/1987  Dougherty ........................... 514/410

OTHER PUBLICATIONS

"Current Topics Porphyrin Phototherapy of Human Cancer"; E. J. Land, pp. 219-223, 1984.
"Hematoporphyria & HPD: Photophysics, Photochemistry and Phototherapy"; Photochemistry and Photobiology vol. 39 No. 6 1984 pp. 851-859.
"Porphyrin Localization and Treatment of Tumors"; Liss 1984 pp. 75-87.
"Biological and Biophysical Properties of the Tumor Localizing Component of Hematoporphyrin Derivative"; David Kessel, May-Ling Cheng Jul., 1985 pp. 3053-3057.
"Determinants of Hematoporphyrin-Catalyzed Photosensitization"; David Kessel, Mar. 1, 1982 pp. 99-101.
"Photodynamic Effects: Porphyrin vs Chlorin"; David Kessel and Christopher J. Dutton; Apr. 3, 1984 pp. 403-405.
"Hematoporphyrin Derivative and Photoradiation Therapy in Early Stage Lung Cancer"; Yoshihiro Hayata et al., pp. 37-47 1984.
"Photophysics of and Instrumentation for Porphyrin Detection and Activation" Daniel Doiron pp. 41-73, 1984.
"Light Dosimetry in Tissue: Application to Photoradiation Therapy"; Daniel R. Doiran, Lars O. Svaasandt and Edward Profio pp. 63-76.
"Porphyrin Derivative: A New Aid for Endoscopic Detection of Malignant Disease"; Lipson et al., pp. 623-629 1961.

Primary Examiner—Richard L. Raymond
Attorney, Agent, or Firm—Arnold S. Weintraub

[57] ABSTRACT

A substance effective for treatment of tumors having a fluorescent emission between 640 nm and 650 nm capable of preferentially localizing in and being retained in tumor cells, the substance being a product of esterification of hematorporphyrin with a chlorin and a process for destruction of tumor cells in a patient involving the steps of:
(a) injecting a solution containing the substance into a patient;
(b) allowing the substance to accumulate in the tumor cells; and
(c) irradiating the tumor site with light at a predetermined intensity and a wavelength between about 640 nm and about 650 nm.

4 Claims, 1 Drawing Sheet

HEMATOPORPHYRIN DERIVATIVE AND METHOD OF PREPARATION AND PURIFICATION

BACKGROUND OF THE INVENTION

1. Field of the Invention:

This invention relates to methods for the preparation and isolation of the specified hematoporphyrin derivatives (HPD) and methods for their use in localization, photosensitization and treatment of tumors. More particularly, this invention relates to methods for the preparation and use of new hematoporphyrin derivatives containing ester-linked chlorins.

2. Background of the Prior Art:

Complex mixtures of porphyrins derived from hematoporphyrin have been cited by Lipson and Baldes as having the ability to localize in neoplastic tissues. See Lipson and Baldes, "Hematoporphyrin Derivative: A New Aid Endoscopic Detection of Malignant Disease", 42 *Journal of Thurasic Cardiovascular Surgery,* 1961, pp 623-629. The resulting photosensitization can catalyze highly selective forms of tumor eradication if a sufficient light flux is provided as reported by Dougherty in Porphyrin Localization and Treatment of Tumors, pp 75-87 (1984); Kessel in "Hematoporphyrin and HPD: Photophysics, Photochemistry and Phototherapy", Photochemical Photobiology, Vol. 39, pp 851-859 (1984); and Land in "Porphyrin Phototherapy of Human Cancer", 46, International Journal of Radiation Biology, pp 219-223 (1984).

An inherent limitation associated with this form of photodynamic therapy is that the production of photodamage in tumor cells requires irradiation of porphyrin-loaded tissues with light at a wavelength that corresponds to one of the porphyrin absorption bands, i.e., 500, 567 and 630 nm. Tissue transparency is known to increase with increasing wave length. Thus, clinical photodynamic tumor eradication preferably takes place at the higher wave lengths such as 630 nm; the weakest of the porphyrin absorption bands.

Thus, as reported in Doiron et al, "Light Dosimetry in Tissue: Application to Photoradiation Therapy" in *Porphyrin Photosensitization,* pp 63-76 (1983) and in "Photophysics and Instrumentation for Porphyrin Detection and Activation" in *Porphyrin Localization and Treatment of Tumors* pp 41-73 (1984), to date photodynamic tumor eradication has been limited by two factors. First, the optical properties of tissues results in substantial scattering and absorption of light. Second, light at 630 nm exhibits weak photoactivating efficiency. It has been found that photodynamic therapy is most effective only when small lesions are treated. See Hayata et al, "Hematoporphyrin Derivative and Photoradiation Therapy in Early State Lung Cancer, *Laser Surgery Medicine, Vol.* 4, pp 39-47 (1984). This phenomenon is related to the decreased photodynamic effect as a function of tissue depth.

Thus, it is highly desirable to devise a tumor localizing photosensitizer drug with a strong absorption in the red spectrum, thereby enhancing the photodynamic toxicity.

It is also desirable that the drug be highly tumor-selective and that the drug be capable of emitting suitable readable chemical characteristics such as fluorescence which will aid in delineating malignancy and in diagnosis.

It is also desirable that a method be provided for preparation and isolation of this drug.

SUMMARY OF THE INVENTION

The present invention is based upon the unexpected discovery that the structure of the hematoporphyrin derivative in clinical use is composed of hematoporphyrin units joined by ester linkages. Synthesis of analogs with more potent photosensitizing ability was thereby shown feasible. The particular derivatives discovered having these characteristics are reaction products of an esterification reaction between a chlorin and hematoporphyrin. In this application, the term "chlorin" is defined as reduced porphyrins including the chlorin derived from mesoporphyrin, and the naturally occurring compound bonellin.

The hematoporphyrin-chlorin ester of the present invention can be synthesized according to the method which comprises the following steps:

(a) admixing chlorin compound in an aqueous alkaline solution having a concentration of an alkali metal hydroxide between about 0.1m and about 0.5m;

(b) admixing hematoporphyrin diacetate to the solution formed in Step A over an interval of between about 2 and about 20 minutes;

(c) allowing the solution to react for a period sufficient to exhaust the chlorin available in solution;

(d) hydrolyzing any unreacted hematoporphyrin diacetate remaining in solution after Step C;

(e) adjusting the acidity of the solution to a pH of 5 after Step C;

(f) isolating the precipitate of the hematoporphyrin-chlorin reaction product formed.

DETAILED DESCRIPTION OF THE INVENTION

Figure 1:
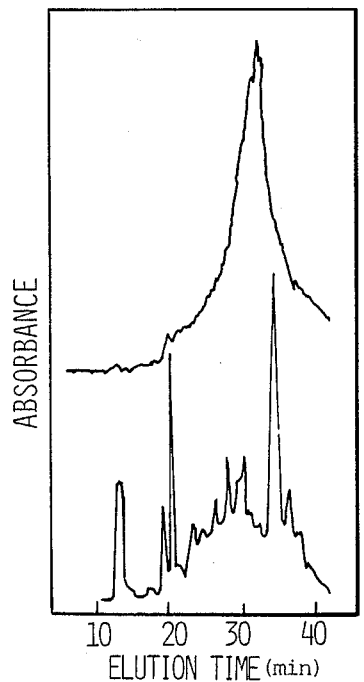
Figure 2:
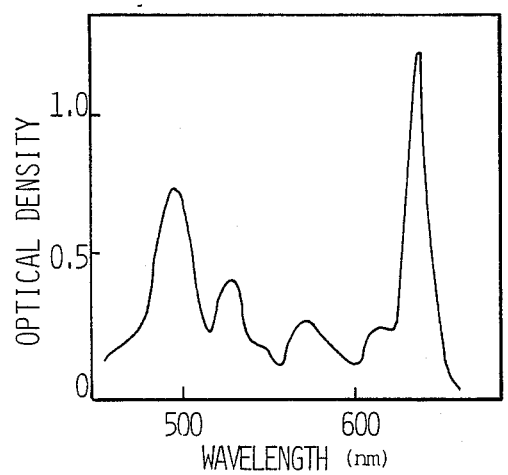
Figure 3:
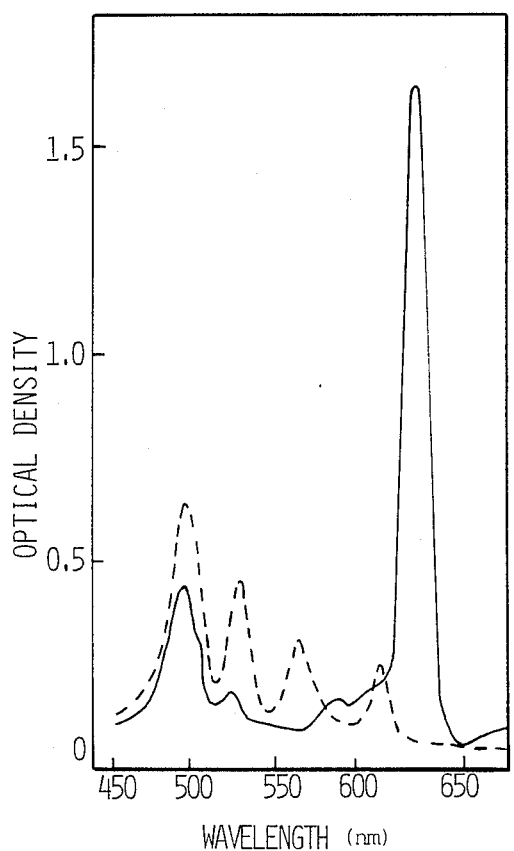
Figure 4:
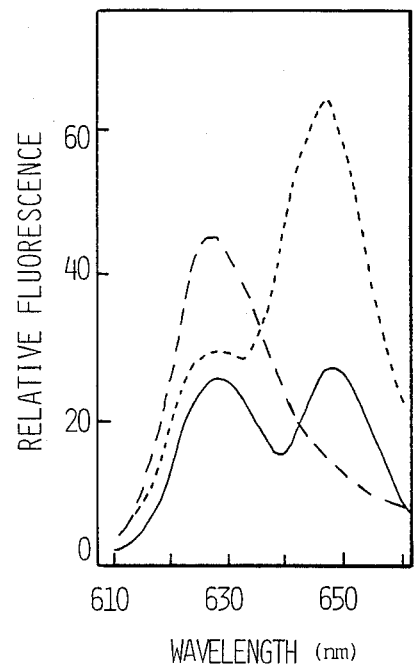

This invention is based on the unexpected discovery that certain newly discovered, synthesized and isolated hematoporphyrin compounds exhibit increased photosensitization and localization in in vivo and in vitro tumor cells. The derivatives of the present invention are reaction products of a chlorin compound selected from the group consisting of bonellin, mesochlorin or mixtures thereof with hematoporphyrin diacetate in an alkaline solution. The material thus formed exhibits a fluorescent emissions at 627 nm and 647 nm upon excitation at 400 nm and absorbance spectrum with peaks at 625 nm and 640 nm.

Without being bound by any theory, it is believed that a hematoporphyrin-chlorin ester is formed by this process and has one of the following structures. Where mesochlorin is esterified with hematoporphyrin it is theorized that the structure of the inventive compound is:

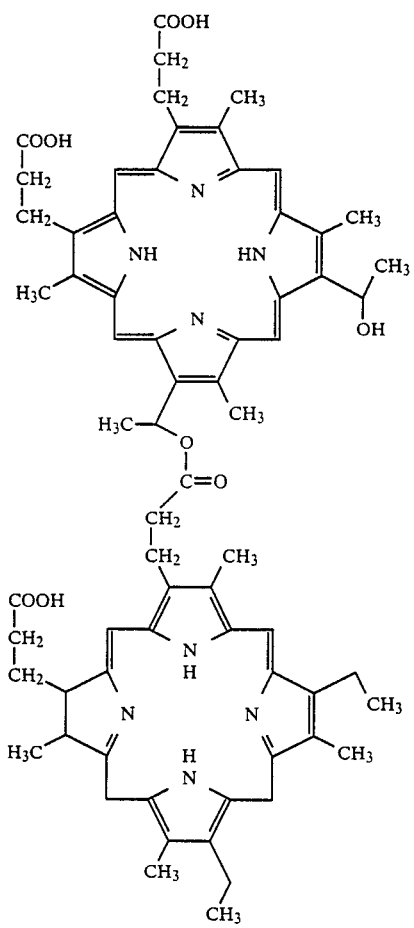

or one of the isomers thereof. Where bonellin is esterified with hematoporphyrin it is theorized that the compound of the present invention is:

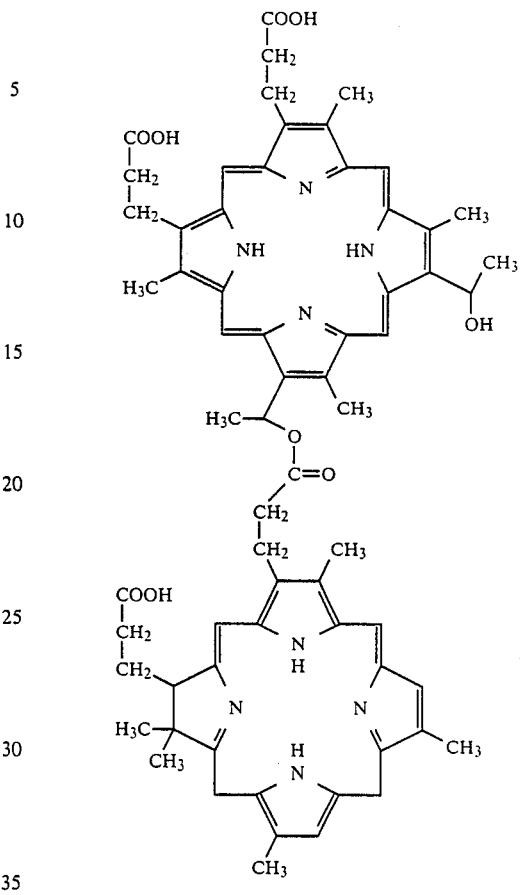

or one of the isomers thereof.

In synthesizing the localizing and photosensitizing agent of the present invention, an aqueous solution containing between about 5 and about 30 parts by weight chlorin per unit of solution is prepared. In the preferred embodiment the solution contains between about 5 and about 15 grams chlorin per liter of solution.

The solution contains an alkaline material in an amount sufficient to provide alkaline material at a concentration between about 0.01 and 0.1 M; preferably between about 0.01 and about 0.1 M. The alkaline material may be any suitable water-soluble basic material. The alkaline material is, generally, selected from the group consisting of alkali metal hydroxides and mixtures thereof. Preferably, the alkaline material is sodium hydroxide. In the preferred embodiment, the chlorin is admixed with the aqueous alkaline solution by rapid stirring in a darkened vessel.

The term "chlorin" as used in the present invention refers to a compound selected from the group consisting of mesochlorin, bonellin, and mixtures thereof. Mesochlorin is the chlorin analogue of mesoporphyrin; also available from Porphyrin Products. Bonellin is a naturally occurring chlorin that or can be synthesized in the manner set forth in Kessel & Dutton. "Photodynamic Effects: Porphyrin vs. Chlorin", *Photochemical Photobiology*, Vol. 40, pp 403-406 (1984), which is herein incorporated by reference.

After addition of chlorin, between about 5 and about 30 parts hematoporphyrin diacetate per unit of solution is added in a mixture interval of between about minutes. The amount of hematoporphyrin added is an amount sufficient to stoichiometrically react with the chlorin present in solution. The stoichiometry of this reaction is believed to be one-to-one. Thus, an amount of hematoporphyrin diacetate equal to the amount of chlorin employed is preferred.

The materials are allowed to react for a period between about 15 and about 120 minutes. To ensure complete and intimate mixture, the solution can be stirred during the reaction interval.

After the reaction interval additional alkaline solution can be added to the reaction mixture in an amount sufficient to hydrolize any unreacted hematoporphyrin diacetate which may remain in the solution. The alkaline solution used for hydrolysis contains an alkaline material selected from the group consisting of alkali metal hydroxides at a concentration between about 0.5N and about 1.0N. The preferred alkali metal hydroxide is sodium hydroxide. The solution added is in an amount between about one-twentieth and about one-fifth of the initial volume of aqueous solution.

After hydrolysis of the hematoporphyrin diacetate, the pH of the solution is adjusted to a level between about 4 and 6; preferably to a level of 5. Adjustment can be made, preferably, by the addition of an aqueous acid such as HCl.

The dimeric reaction product can be isolated using suitable fractional column chromatographic techniques. In the preferred embodiment, preparative fractionation of the reaction product can be carried out on columns of Sephadex LH-20 available from Pharmacia, of Piscataway, NJ. The columns were eluted with an elutant containing tetrahydrofuran, a short chain alcohol and an aqueous solution buffered between 6.5 and 7.5 in a ratio of 2:1:1 respectively. The alcohol chosen is preferably methanol while the aqueous solution contains a phosphate buffer capable of maintaining the pH at approximately 7.

In the preferred embodiment, it has been found that a 5 x 30 cm column can fractionate up to about 100 mg of hematoporphyrin reaction product applied in approximately 40 ml of solvent. As can be appreciated by those skilled in the art of fractional column chromatography, the size of the column can be varied to accommodate amounts of reaction product to be separated.

In the method of the present invention, the first fraction eluted has been found to contain the hematoporphyrin ester. This fraction can be collected and evaporated under reduced pressure. The evaporated material can be effectively stored in the dark at a temperature between about 0° C. and about 20° C. When use is desired, the material can be dissolved in an aqueous solution buffered to a pH between about 7.0 and about 8.0. Suitable buffers are selected from the group consisting of alkali metal carbonates and mixtures thereof.

In employing the compound of the present invention, a suitable intravenous solution can be prepared containing the compound. The concentration of the drug in the solution is an amount sufficient to render a dosage of between about 1 mg/kg of body weight and 10 mg/kg of body weight.

After injection, sufficient time is allowed to elapse to permit uptake of the drug by tumor cells. This interval is preferably between about 1 and about 3 days. The tumor site is then irradiated with light having an appropriate intensity and a wave length between about 640 nm and about 650 nm.

It is to be understood that the compound of the present invention can also be employed in a variety of tumor-cell eradication procedures using irradiation treatment known to those skilled in the art.

EXAMPLE I

A 500 µl solution of 0.1 M NaOH containing 10 mg mesochlorin was rapidly stirred in the dark. The mesochlorin employed was obtained from Porphyrin Products. Ten milligrams of solid hematoporphyrin diacetate was added over a period of five minutes. The hematoporphyrin diacetate employed was prepared by the method set forth in Kessel and Dutton "Photodynamic Effects: Porphyrin vs. Chlorin" *Photochemical Photobiology*, Vol. 40, pp 403–406 (1984), which is herein incorporated by reference.

After 60 minutes, an additional 50 µl of 1 N NaOH was added to hydrolyze any unreacted hematoporphyrin diacetates remaining in solution. The solution was brought to pH 5 by addition of 0.1 N HCl to a total volume of 1 ml with water. The material thus formed was isolated using the technique discussed in Kessel and Cheng, "Biological and Biophysical Properties of the Tumor Localizing Component of Hematoporphyrin Derivative", *Cancer Research*, Vol. 45, pp 3053–3057, (1985) which is herein incorporated by reference.

The first fraction, shown by HPLC analysis to contain <1% hematoporphyrin or chlorin, was evaporated under pressure and stored at −20° C. in the dark. For use in biological studies, this fraction was dissolved in 0.1 M Na2CO3 and brought to pH 7.5 with 0.1 MHCl. This material designated as CHE (chlorin-hematoporphyrin ester).

EXAMPLE II Analysis of Reaction Products Formed in Example I

High pressure liquid chromatographic analysis of crude and purified CHE preparations was performed using a C-8 column and CN guard column in a Waters Z-module system. The column was eluted with a 30 minuted gradient of 70–100 percent methanol (remainder aqueous 5mM butyl ammonium phosphate, pH 3.5). The flow rate was 1 ml/min. After 30 minutes, the flow rate was increased to 1.5 ml/min. and the column was eluted with methanol for an additional 15 minutes with absorbance of the elevate monitored at 395 nm. The elution tracing is shown in FIG. I lower tracing.

Elution times of known components of the crude mixture are hematoporphyrin at 13.2 minutes, hydroxyethylvinyldeuteroporphyrin (2 isomers) at 19.8 and 20.8 minutes; protoporphyrin at 28.5 minutes and mesochlorin (2 isomers) at 34.5 and 36.3 minutes. The tumor localizing fraction elutes as a broad band between 22 and 40 minutes.

Purified CHE obtained by non-aqueous gel (CH-20) exclusion chromatography is shown as the top tracing in FIG. I.

Absorbance spectra for purified CHE was carried out in a 2:1:1 mixture of tetrahydrofuran; methanol; aqueous 5mM phosphate buffer pH 7 using Perkin-Elmer Model 552 dual beam spectrophotometer. The concentration of CHE employed was 7.5 gl/ml. This spectra is shown in FIG. II. The CHE exhibits a weak porphyrin absorption band at 630 nm and a much stronger absorption by the chlorin moiety at 640 nm.

Absorbance spectra of 10 µM hematoporphyrin (dashed line) and mesochlorin (solid line) in tetrahydrofuran: methanol: aqueous buffer were also obtained and are shown in FIG. III. These results, when compared to the tracing in FIG. II suggest that CHE prepared according to the method of the present invention contains an approximately equal ratio of porphyrin to chlorin.

The fluorescence emission spectrum of CHE was determined using a sample of CHE dissolved in tetrahydrofuran: methanol: aqueous buffer analyzed with a Perkin-Elmer MPF 44B fluorometer and is shown as a solid line in FIG. II. Upon excitation at 400 nm, fluorescence emission of the porphyrin moiety at 627 nm and of the chlorin moiety at 647 nm were observed. Identical fluorescence yields were obtained for hematoporphyrin and mesochlorin. This supports the proposition that CHE contains an approximately equal ratio of porphyrin to chlorin.

EXAMPLE III

The synthetic procedure of Example I was repeated with bonellin being substituted for mesochlorin. This material was analyzed according to the methods set forth in Example II and exhibited analytical and spectral properties almost identical to those shown in FIGS. I to IV except that the HPLC retention tie of bonellin was found to be 26.3 minutes.

EXAMPLE IV

The storage stability of aqueous solutions of CHE (ph 7.5) is determined at −20° C. and at 4° C. respectively. The samples stored at −20° C. remained stable. However, samples stored at 4° C. exhibit gradual hydrolysis of the ester-linkage.

EXAMPLE V

Dihematoporphyrin ester (DHE), the tumor-localizing component of hematoporphyrin derivatives was isolated according to the procedures set forth in the Kessel reference discussed in Example I.

In order to determine the photosensitization capacity of DHE and CHE, respectively, comparison in vitro tests were prepared using L1210 mouse/leukemia cells grown in culture using Fischer's medium plus 10 percent horse serum. Cell suspensions (7 mg/ml wet weight) were incubated for 24 hours in growth medium containing the 5 g/ml of the respective photosensitizer. The cell suspensions were, then, washed for 30 minutes at 37° C. in fresh medium to remove readily diffusible porphyrins.

Uptake of DHE or CHE, purified by gel-exclusion chromatography, was measured by extraction of cells after 24 hour incubations in vitro. Cell pellets (20-30 mg) were suspended in 800 μL of phosphate buffer (pH 3.5) and shaken for 3 minutes with 2 ml of a 1:1 mixture of methanol: chloroform. The lower phase was collected by centrifugation and used for measurement of absorbance at 400 nm. No fluorescence was detectible at the interface or in the upper phase.

Irradiation was carried out for five minutes (fluence =2000 J/m$^2$) using a 100 w tungsten-halogen lamp with a wave length selected via narrow bandpass interference filters (=10 nm). Photodynamic effects on cell viability, as a function of irradiation wavelength, were measured by a soft-agar clonogenic assay in the manner described in Kessel, "Determinants of Hematoporphyrincatalyzed Photosensitization" 36 *Photochemical Photobiology* pp. 99–101 (1982) which is incorporated herein by reference. Light filters were purchased from the Oriel Corp. of Stanford, CT, and the light flux was measured with a thermopile obtained from the same source.

Studies on photodynamic cytotoxicity of cells treated with CHE or DHE for 24 hours indicated that the action spectrum of the porphyrin derivatives was different from that of the chlorin-porphyrin ester as shown in the data collected in Table I. The optimal phototoxic light wave length for cells loaded with DHE was 630 nm; with CHE, 640. The more effective photosensitization by the chlorin derivative is also shown. As shown in Table I, at a constant flux of 2000-J/M$^2$, CHE was 5-fold more lethal than DHE.

EXAMPLE VI

In vitro uptake of DHE, CHE and HPD, hematoporphyrin, mesochlorin and bonellin by tumor cells was studied using L1210 cells incubated for 24 hours with 10 μg/ml concentrations of each respective compound. The cells were then washed for 30 minutes in fresh medium at 37° C. and drug concentrations were determined. The results are set forth in Table II.

As can be seen from these results, the accumulation of DHE and CHE are almost identical. HDP accumulation is almost ½ that amount; while the in vitro uptake and accumulation of the other compounds was significantly less than that of DHE or CHE.

EXAMPLE VII

In vivo biological studies were conducted using DHE, CHE, HPD, hematoporphyrin, mesochlorin and bonellin. The Lewis lung tumor was maintained in female C57BL/6 mice by S.C. implant. Seven days after implantation, a respective compound was administered to test mice by i.p. injection at a dosage level of 5 mg/kg. Forty-eight hours after injection, each tumor was excised, weighed and homogenized in 50 mM 4-(2-hydroxyethyl)-1-piperazineethanesulfonic acid buffer (pH7) containing 10 mM cetyltrimethyl ammonium bromide (1 m./100 mg tissue). The resulting homogenates were shaken with 2.5 volumes of methanol: chloroform (1:1) and the phases separated by centrifugation. Under these conditions, fluorescence is quantitatively extracted into the chloroform-rich phase. These extracts were used for determination of fluorescence emission spectra (excitation wave length, 400 nm). Tumor localizing porphyrins present in such extracts have reduced fluorescence yields. For analytical studies, the extracts were evaporated and the residue hydrolyzed in 0.5 M HCl at 37° C. for 18 hours. This results in quantitative conversion of oligomers to monomers so that fluorescence measurements will provide an accurate estimate of photosensitizer levels.

Administration of HDP, DHE or CHE to mice bearing Lewis lung tumor led to accumulation of fluorescent components at tumor loci as shown in Table III. Administration of hematoporphyrin, mesochlorin or bonellin in vivo led to no detectable concentration of fluorescent products at tumor loci.

A comparison of drug concentrations in skin to that in the tumor indicates that tumor concentrations was three times that in the skin.

Analysis of fluorescence emissions on the various tumor extracts indicated that administration of CHE led to greater tumor fluorescence emission at 647 nm than at 627 nm. Administration of HPD or the tumor-localizing fraction of HPD led to fluorescence at 627 nm only as shown in FIG. IV.

TABLE I
ACTION SPECTRA OF THE DHE AND CHE

| Drug | Wavelength (nm) | | | |
|------|-----|-----|-----|-----|
| | 620 | 630 | 640 | 650 |
| HPD | 83 + 4[a] | 58 + 4 | 94 + 3 | 98 + 2 |
| DHE | 68 + 4 | 45 + 2 | 85 + 5 | 96 + 3 |
| CHE | 96 + 5 | 87 + 5 | 10 + 2 | 65 + 2 |

[a]Mean + SD of control percentage.

TABLE II
UPTAKE OF PHOTOSENSITIZERS IN VIVO AND IN VITRO

| Drug | Uptake in vitro g/100 mg cells | Uptake in vivo g/g cells |
|------|------|------|
| Hematoporphyrin | <0.01 | <0.01 |
| Mesochlorin | 0.05 + 0.01[a] | <0.01 |
| Bonellin | 0.06 + 0.01 | <0.01 |
| HPD | 0.22 + 0.03 | 1.1 + 0.2 |
| DHE | 0.49 + 0.03 | 2.1 + 0.4 |
| CHE | 0.43 + 0.02 | 2.4 + 0.3 |

[a]Average + SD of three determinations.

I claim:
1. A substance effective for treatment of tumor cells having a fluorescent emission between 640 and 650 nm and capable of preferentially localizing in and being retained in tumor cells over normal cells, the substance selected from the group consisting of:

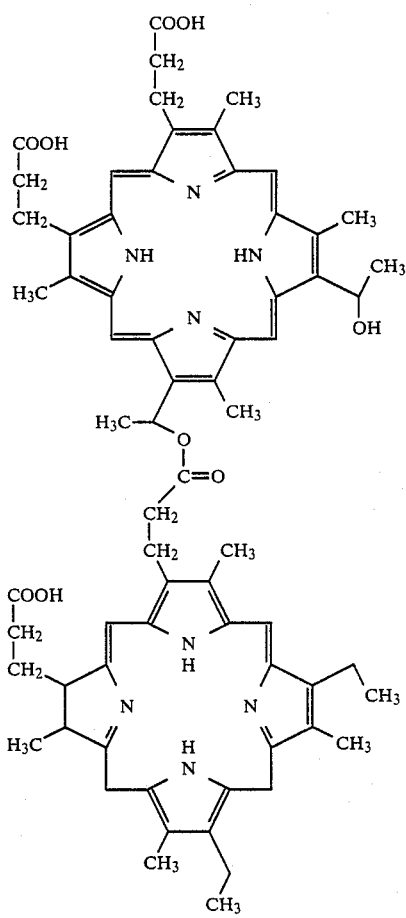

and its isomers;

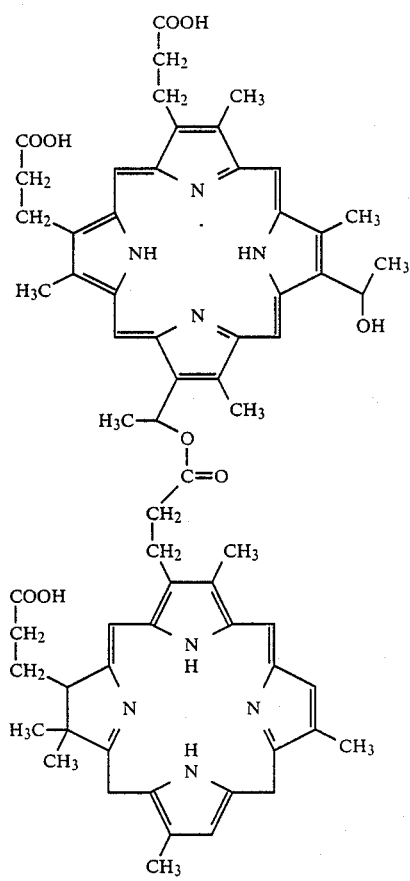

and its isomers;
II. the alkali metal salts thereof; and mixtures thereof;
IV. the alkali metal salts thereof; and mixtures thereof;

2. A process for the production and purification of the substance of claim 1 comprising the steps of:
 (a) admixing a chlorin which is a reduced porphyrin selected from the group consisting of: mesochlorin, bonellin and mixtures thereof, in an aqueous alkaline solution having a concentration of an alkali metal hydroxide between about 0.05 and about 0.5 M;
 (b) adding an amount of hematoporphyrin diacetate to the solution formed in Step A, the hematoporphyrin being added over an interval of between two and twenty minutes;
 (c) allowing the solution to react for a period sufficient to exhaust the chlorin available in solution;
 (d) hydrolyzing any unreacted hematoporphyrin diacetates remaining in solution after the reaction period of Step C;
 (e) adjusting the acidity of the solution to a pH of 5 after the reaction period of Step C;
 (f) maintaining ambient temperatures throughout the process; and
 (g) isolating the reaction product of esterification of hematoporphyrin with chlorin as a result of Steps a through f.

3. The process of claim 2 wherein the chlorin is admixed in an aqueous solution containing sodium hydroxide.

4. The process of claim 2 wherein the hydrolyzing step comprises adding a portion of aqueous sodium hydroxide to the reaction mixture.

* * * * *